United States Patent
Webb et al.

(10) Patent No.: US 6,629,533 B1
(45) Date of Patent: *Oct. 7, 2003

(54) PUNCTUM PLUG WITH AT LEAST ONE ANCHORING ARM

(75) Inventors: Nicholas J. Webb, Redding, CA (US); Richard W. Mendius, Collierville, TN (US)

(73) Assignee: Eagle Vision, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/608,463

(22) Filed: Jun. 30, 2000

(51) Int. Cl.⁷ .............................................. A61B 17/00
(52) U.S. Cl. .......................................... 128/887; 604/8
(58) Field of Search ................. 128/846, 848, 128/887; 604/8–10, 294

(56) References Cited

U.S. PATENT DOCUMENTS

| | | | |
|---|---|---|---|
| 3,949,750 A | 4/1976 | Freeman | 128/260 |
| 4,056,496 A | 11/1977 | Mancini et al. | 260/29.6 |
| 4,461,295 A | 7/1984 | Herrick | 128/303 |
| 4,660,546 A | 4/1987 | Herrick et al. | 128/1 R |
| 4,886,488 A | 12/1989 | White | 604/9 |
| 4,915,684 A | 4/1990 | MacKeen et al. | 604/8 |
| 4,959,048 A | 9/1990 | Seder et al. | 604/9 |
| 5,049,142 A | 9/1991 | Herrick et al. | 604/294 |
| 5,171,270 A | 12/1992 | Herrick | 623/11 |
| 5,283,063 A | 2/1994 | Freeman | 424/427 |
| 5,334,137 A | 8/1994 | Freeman | 604/8 |
| 5,417,651 A | 5/1995 | Guena et al. | 604/8 |
| 5,423,777 A | 6/1995 | Tajiri et al. | 604/294 |
| 5,522,837 A | 6/1996 | Latina | 606/201 |
| 5,601,553 A | 2/1997 | Trebing et al. | 606/61 |
| 5,626,559 A | 5/1997 | Solomon | 604/9 |
| 5,645,565 A | 7/1997 | Rudd et al. | 606/213 |
| 5,723,005 A | 3/1998 | Herrick | 623/4 |
| 5,766,243 A | 6/1998 | Christensen | 623/4 |
| 5,830,171 A | 11/1998 | Wallace | 604/8 |

FOREIGN PATENT DOCUMENTS

| | | |
|---|---|---|
| GB | 2069339 A | 8/1981 |
| GB | 2160778 A | 1/1986 |

*Primary Examiner*—Michael A. Brown
(74) *Attorney, Agent, or Firm*—Gordon & Jacobson, P.C.

(57) ABSTRACT

A punctum plug generally includes a shaft and a head at a proximal end of the shaft. The shaft is provided with at least one circumferentially radiating flexible anchoring arm of varying radial extension at at least two locations along its length which is adapted to secure the punctum plug within the punctum of a wearer. The head has a concave proximal surface and a distal surface which tapers toward the shaft. A diameter of the head is substantially larger than a diameter of the shaft. According to a first embodiment of the invention, a plurality of anchoring arms in the form of symmetric circumferential rings are spaced a distance apart along a length of the shaft and define spaces therebetween. One or more of the rings has a diameter equal to or larger than the diameter of the head of the plug, and different rings preferably have different diameters. According to a second embodiment of the invention, a plurality of anchoring arms in the form of longitudinally offset flanges are spaced a distance apart along a length of the shaft. The offset flanges are offset relative to a plane extending axially through the shaft.

37 Claims, 6 Drawing Sheets

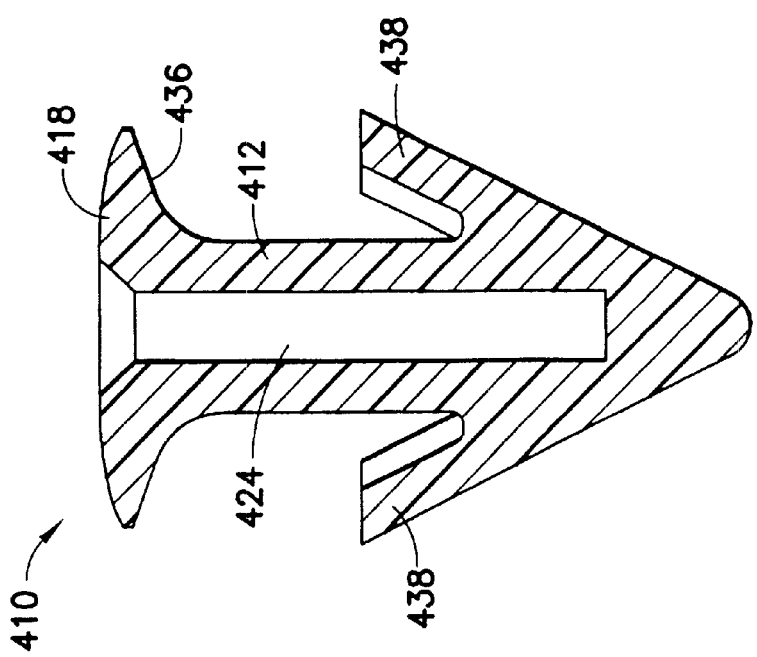
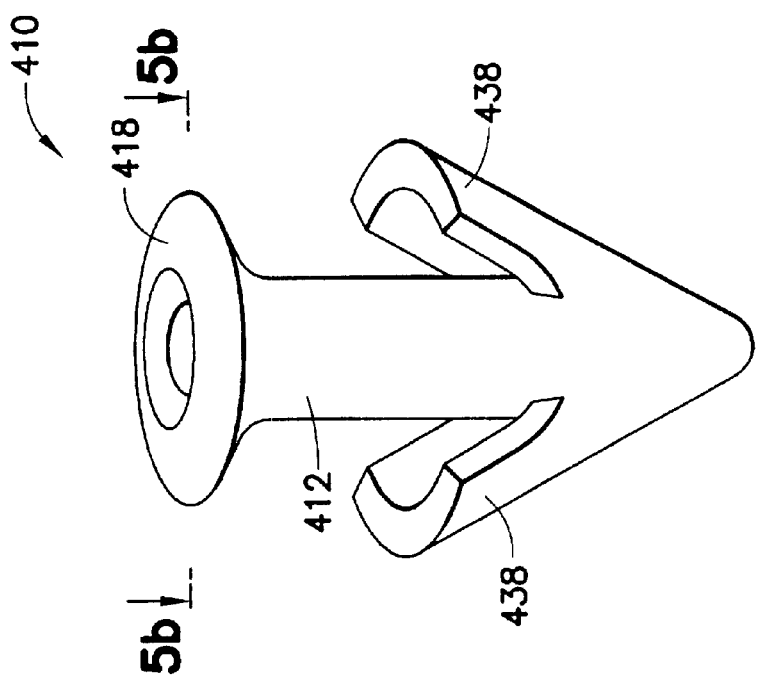

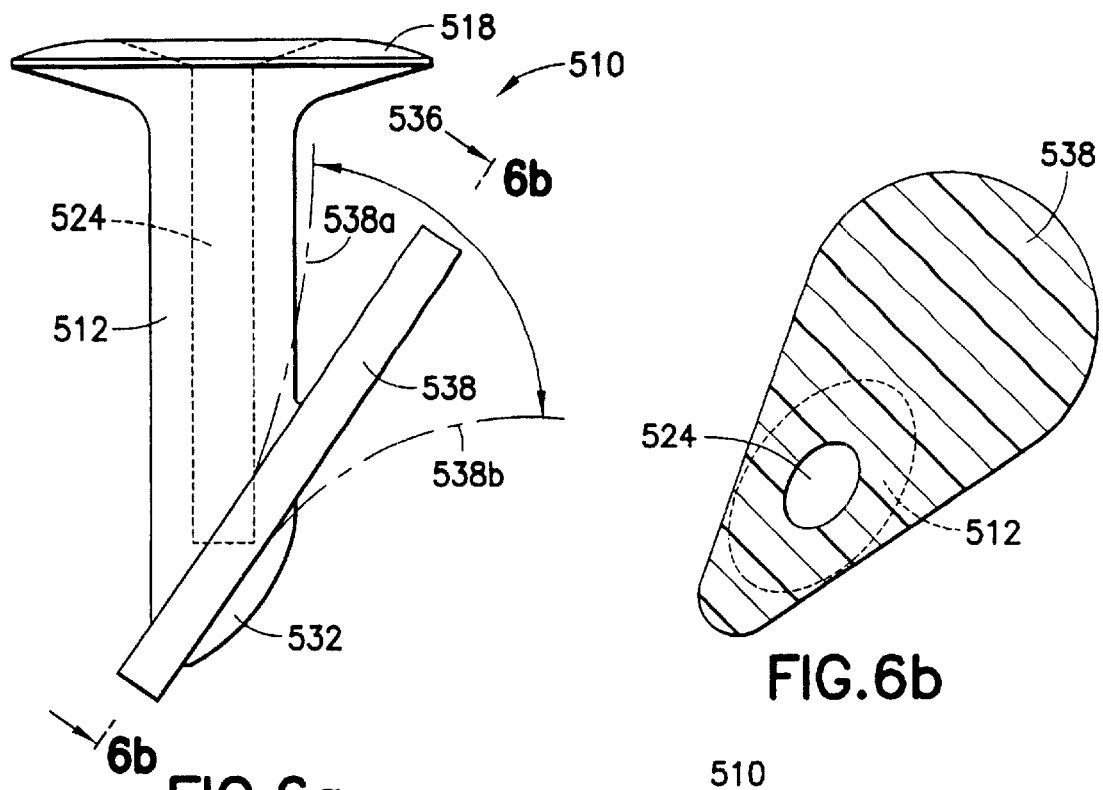
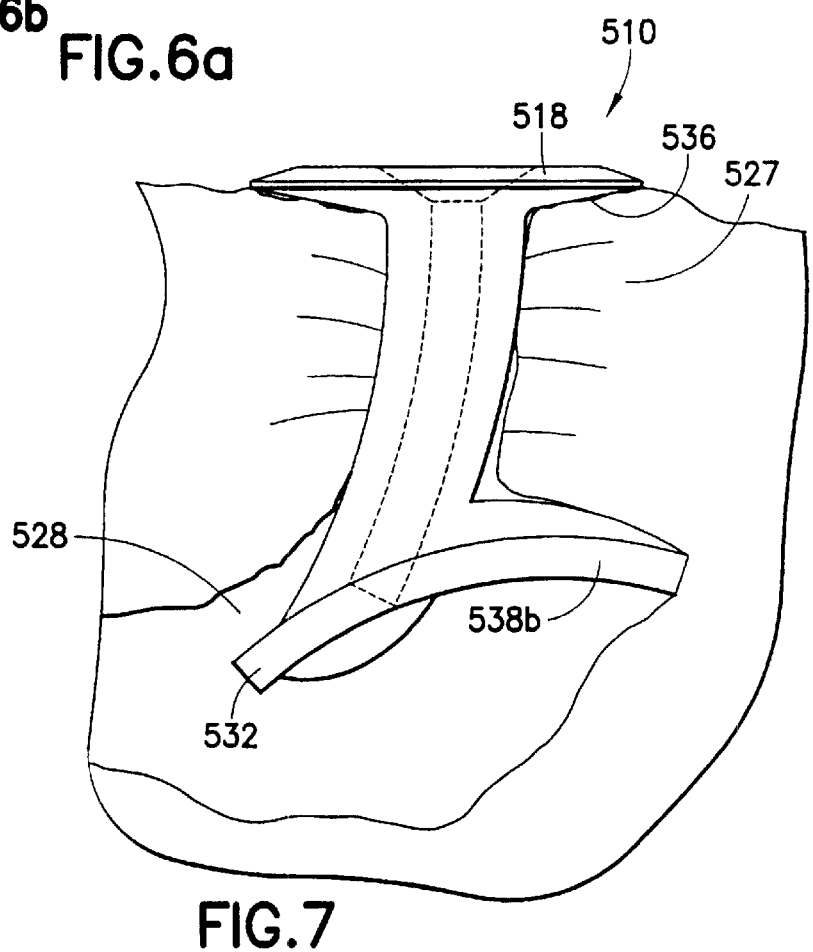

PUNCTUM PLUG WITH AT LEAST ONE ANCHORING ARM

This application is related to U.S. Pat. No. 6,041,785, and is a continuation-in-part of U.S. Ser. No. 09/305,599 filed May 5, 1999, which in turn is a continuation-in-part of Ser. No. 08/826,216 filed Mar. 27, 1997; all three of which are hereby incorporated by reference herein in their entireties.

BACKGROUND OF THE INVENTION

1. Field of the Invention

This invention relates broadly to medical canalicular inserts. More particularly, this invention relates to canalicular plugs which are placed into the punctal opening of the lacrimal duct to prevent lacrimal fluid from flowing through the lacrimal duct.

2. State of the Art

A variety of eye problems are related to an insufficient volume of tears on the surface of the eyes. The most common is keratoconjunctivitis sicca, also known as dry eyes. Contact lens problems are also often provoked by a lack of tear volume. A common cause for the insufficient tear volume is the drainage of tear fluid through the punctal opening of the lacrimal duct and into the nasal passage, thereby removing the fluid from where it is needed at the eye surface. Furthermore, drainage of tear fluid through the lacrimal duct into the nasal passage is believed to be the cause of or associated with several additional problems such as post nasal drip, sinusitis, allergies, headaches, and snoring.

A number of methods for closing the punctal opening have been used to prevent drainage of tears through the lacrimal duct, including suturing, laser sealing, and plugging. Plugging with a canalicular plug, such as a punctum plug or a lacrimal plug, is the least severe solution, is relatively inexpensive, and is being performed with increasing frequency.

Referring to prior art FIG. 1, a punctum plug 10 typically includes an elongate member or shaft 12 having a proximal end 14 and a distal end 16, a head 18 at the proximal end 14 of the shaft 12, and a relatively larger body 20 at the distal end 16 of the shaft 12 for occluding a lacrimal duct 22. The plug 10 is usually provided with a proximal axial bore 24 for receiving an insertion tool. In the punctum plug insertion procedure, the insertion tool is positioned into the bore 24 of the plug 10, the body 20 of the plug 10 is directed at a punctal opening 26 of the lacrimal duct 22, and force is applied to the insertion tool to move the body 20 of the plug 10 through the punctal opening 26, the muscles of the punctal ring 27, and into the vertical punctum 28 of the lacrimal duct 22. Once the plug 10 is fully inserted in the punctum 28, the insertion tool is removed. The plug 10 is fully inserted when the head 18 seats against the tissue at the punctal opening 26 and the body 20 seats within the lacrimal duct 22 so as to block the passage of tear fluid into the duct 22 and thereby retain tear fluid at the surface of the eye. Similarly, lacrimal plugs (not shown) which seat entirely within the lacrimal duct (completely below the punctal opening) are also known.

It has been found that prior art punctum and lacrimal plugs, while providing some benefit, often do not provide satisfactory occlusion of the lacrimal duct. Tear fluid tends to flow through the interstices 30 between the body of the plug and the tissue of the vertical punctum of the lacrimal duct. One proposed prior art solution of this problem has been to provide the plug 10 with an enlarged distal body 20. However, the punctum plug having the larger distal body is difficult to insert through the relatively small punctal opening and may inadvertently cause damage to the delicate punctal tissue.

Another problem with prior art punctum plugs is that the puncta of different individuals tend to be different in size. Thus, a physician is required to have available a plurality of differently sized punctum plugs. The physician must carefully measure or estimate :the size of the punctum and punctal opening of each patient to select the proper sized plug to insert. If the physician misjudges the size required, the punctum plug will not effectively block the lacrimal fluid flow and the patient will not realize the full benefit of the device.

SUMMARY OF THE INVENTION

It is therefore an object of the invention to provide a punctum plug which occludes the flow of tears through the lacrimal duct.

It is another object of the invention to provide a punctum plug which is not easily unintentionally dislodged from the lacrimal duct.

It is also an object of the invention to provide a punctum plug which is designed to facilitate insertion into the lacrimal duct.

It is a further object of the invention to provide a punctum plug which can easily be extricated by a physician when desired.

It is yet a another object of the invention to provide a single sized punctum plug which is adaptable to fit within substantially all sized puncta.

In accord with these objects, which will be discussed in detail below, a punctum plug generally includes a shaft and a head at a proximal end of the shaft. The distal end of the shaft terminates at a tip. The shaft is provided with at least one circumferentially radiating flexible anchoring arm of varying radial extension at at least two locations along its length which is adapted to secure the punctum plug within the punctum of a wearer.

The punctum plug of the invention is preferably made from a highly flexible, resilient biocompatible material. According to the invention, the head has a concave proximal surface and a distal surface which tapers toward the shaft. A diameter of the head of the plug is substantially larger than a diameter of the shaft. Preferably, the at least one flexible anchoring arm radially extends a distance greater than a radial width of the head. In accord with a first preferred aspect of the invention, the tip is no greater in diameter than the diameter of the shaft. An axial insertion bore is optionally defined through the proximal head of the plug extending a distance through the shaft.

According to a first embodiment of the invention, a plurality of anchoring arms in the form of symmetric circumferential rings are spaced a distance apart along a length of the shaft and define spaces therebetween. One or more of the rings has a diameter equal to or larger than the diameter of the head of the plug, and different rings preferably have different diameters.

According to a second embodiment of the invention, a plurality of anchoring arms in the form of longitudinally offset flanges are spaced a distance apart along a length of the shaft. The offset flanges are offset relative to a plane extending axially through the shaft providing an asymmetric cross-section to the plug at the shaft. Preferably, the flanges radially extend different lengths away from the shaft.

According to a third embodiment of the invention, the anchoring arm is a single flange helically wound about the shaft, and optionally the tip of the punctum plug. The radial length of the helical flange changes as it moves up or down the shaft. In addition, the pitch of the helical flange may change along the shaft.

According to a fourth embodiment of the invention, two preferably arcuate anchoring arms are provided at a distal portion of the shaft and extend outward and towards the head. The anchoring arms thereby function as barbs which retain the plug within the punctum.

According to a fifth embodiment of the invention, a single anchoring arm extends from the tip of the plug outward and upward toward the head of the plug. In addition, the arm is preferably relatively small adjacent the tip, to aid in insertion, and generally becomes relatively larger with its distance from the tip. The anchoring arm is flexible, and adapted to engage the underside of the punctal ring to secure the plug within the punctum.

In all embodiments, it is preferred that the arm or arm portion which extends the furthest radially be located at or along a middle portion of the shaft.

According to the invention, prior to insertion of the punctum plug into the punctum of a wearer, the punctal opening of the eye is optionally dilated. The plug is advanced into the punctum until the head of the plug rests adjacent the punctal opening. When the punctal opening returns to its predilated size, the anchoring arm or arms retain the punctum plug within the punctum and the head occludes the opening preventing lacrimal fluid flow. The anchoring arm or arms and the head surround the punctal ring to create a secure fit.

Additional objects and advantages of the invention will become apparent to those skilled in the art upon reference to the detailed description taken in conjunction with the provided figures.

BRIEF DESCRIPTION OF THE DRAWINGS

FIG. 2b is an enlarged cross-sectional view of the first embodiment of the punctum plug according to the invention taken along line 2b—2b of FIG. 2a;

FIG. 3b is an enlarged cross-sectional view of the second embodiment of the punctum plug according to the invention taken along line 3b—3b of FIG. 3a;

FIG. 4b is an enlarged cross-sectional view of the third embodiment of the punctum plug according to the invention taken along line 4b—4b of FIG. 4a;

FIG. 5a is a perpsective view of a fourth embodiment of a punctum plug according to the invention;

FIG. 5b is a cross-sectional view of the fourth embodiment of the punctum plug according to the invention taken across line 5b—5b in FIG. 5a;

FIG. 6a is a side elevation view of a fifth embodiment of the punctum plug according to the invention;

FIG. 6b is a cross-sectional view of the fifth embodiment of the punctum plug according to the invention taken across line 6b—6b in FIG. 6a; and FIG. 7 illustrates the fifth embodiment of the punctum plug inserted within a punctum.

DETAILED DESCRIPTION OF THE PREFERRED EMBODIMENTS

Figure 1:
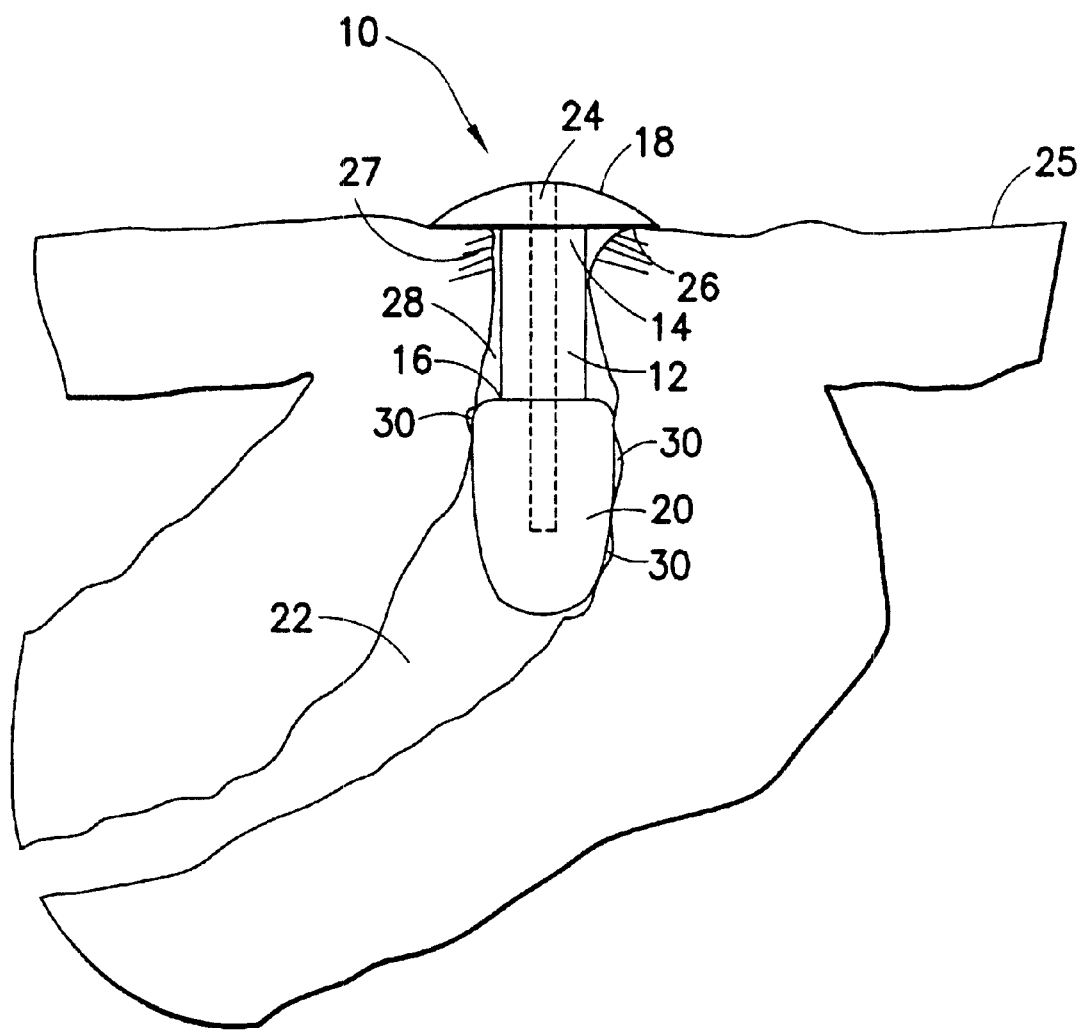
FIG. 1 is a broken perspective view of a prior art punctum plug inserted within a punctum of a patient.
Figure 2B:
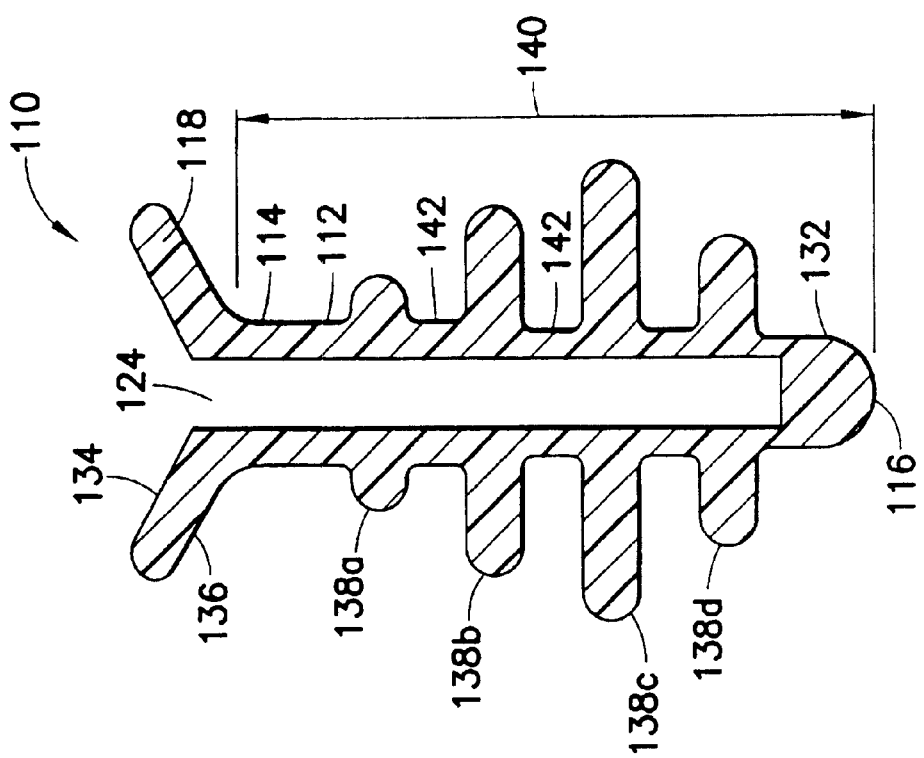
Figure 2A:
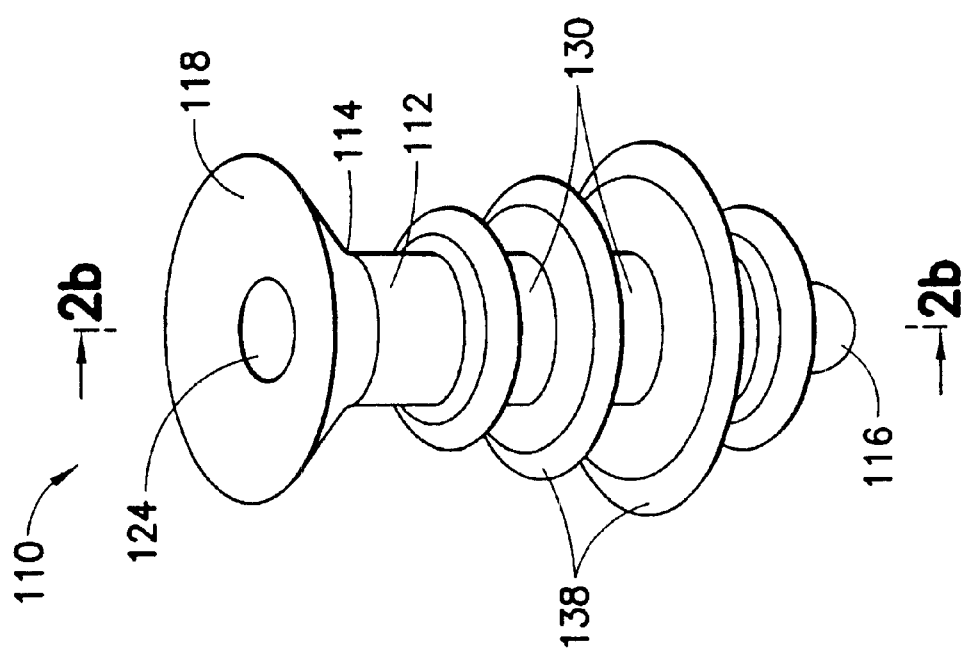
FIG. 2a is a perspective view of a first embodiment of a punctum plug according to the invention.

Turning now to FIGS. 2a and 2b, a punctum plug 110 according to the a first embodiment of the invention is provided which generally includes a shaft 112 having a proximal end 114 and a distal end 116, and a head 118 at the proximal end 114 of the shaft 112. The shaft 112 terminates in a tip 132 at its distal end 116. According to the invention, the shaft 112 is preferably substantially cylindrical. The head 118 preferably has a concave proximal surface 134, a distal surface 136 which tapers toward the shaft 112, and a diameter greater than a diameter of the shaft 112. An optional axial insertion bore 124, adapted to receive an insertion tool (not shown), is defined through the head 118 of the plug 110 extending a distance through the shaft 112. The punctum plug 110 of the invention is preferably molded from a resilient biocompatible material such as silicone or another soft, low Durometer biocompatible material which is highly flexible and permits the head 118 to conform to the shape of a variety of sized and shaped punctal openings.

In accord with the first embodiment of the invention, the shaft 112 is provided at at least two locations along its length a circumferentially radiating anchoring arm 138. The anchoring arms 138 are flexible yet are adapted to frictionally or mechanically engage punctal tissue to secure the plug 110 within a punctum of a wearer. By providing anchoring arms of different radial lengths, differently sized puncta are accommodated. Preferably, at least one of the flexible anchoring arms 138c extends radially from the shaft 112 a distance greater than a radially extended distance of the head 118. The largest anchoring arm 138c aids in retention of the plug 110 within even the largest punctum, yet is adapted to fold to fit smaller punctum. Although the anchoring arms can act to restrict some of the lacrimal fluid flow within the punctum, according to the invention, punctal lacrimal flow occlusion mainly occurs as a result of tissue at the punctal opening seating about the distal surface 136 of the head 118. The punctum plug of the invention properly fits within a variety of sized puncta resulting in the ability to use a punctum plug of one size to achieve improved lacrimal flow occlusion in a variety of sized puncta.

In accord with a preferred aspect of the invention, the tip portion 132 of the shaft 112, which may be rounded, truncated, or pointed, is no larger in diameter than a diameter of the shaft 112 resulting in a reduced distal surface area relative to prior art plugs 10. The reduced distal surface area aids in insertion and prevents build-up of pressure behind the plug 110 reducing the likelihood of inadvertently dislodging the plug 110. In addition, the smaller tip results in reduced tissue damage during insertion and greater comfort for the patient.

Particularly with respect to the first embodiment 110 of the invention, the anchoring arms 138 constitute a plurality of circumferential rings 138 spaced a distance apart along a length 140 of the shaft 112 defining spaces 142 therebetween. The rings 138 are symmetric about a plane extending axially through the shaft 112. Preferably, four rings 138a–138d are positioned substantially equidistance apart along the shaft 112. The rings 138a–138d differ in radially extension, i.e., the diameter of each ring is different. As stated above, preferably, at least one of the anchoring rings (138c) has a diameter greater than the diameter of the head 118 of the plug 110. It should be appreciated that each of the arms is sufficiently flexible such that the arms will fold upward toward the head during insertion and will accommodate even unusually narrow punctal openings.

Figure 3B:
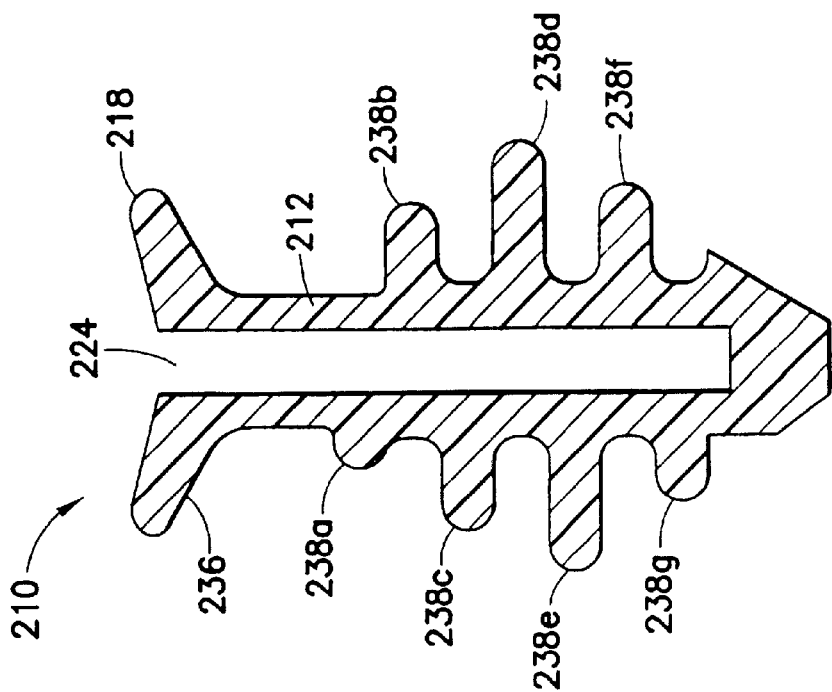
Figure 3A:
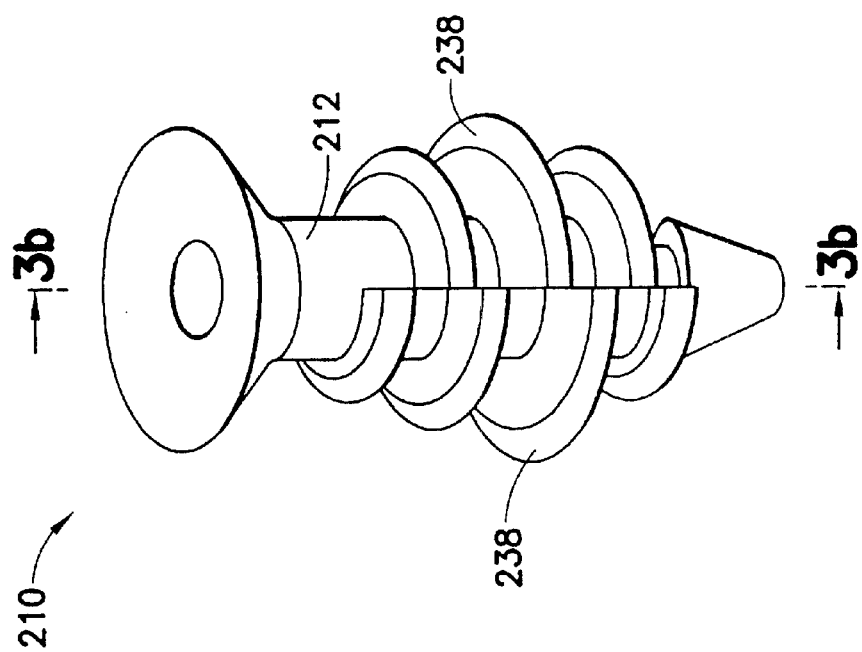
FIG. 3a is a perspective view of a second embodiment of a punctum plug according to the invention.

Referring to FIGS. 3a and 3b, a second embodiment of a punctum plug 210, substantially similar to the first embodiment 110 (with like parts having numbers incremented by 100) is shown. According to the second embodiment 210, the anchoring arms 238a–238g are a plurality of longitudinally offset flanges, at least some of which have different radial lengths spaced a distance apart along a length of the shaft 212. The flanges 238a–238g are all substantially semicircular with two groups of three flanges being offset relative to each other with respect to a plane of the plug 210 extending axially through the shaft 212. Thus, the flanges provide an asymmetric cross-section along a plane of the plug 210. As with the first embodiment, it is preferable that at least one of the flanges 238 (e.g. 238d and 238e) extends radially outward a distance greater than the radial extension of the head 218.

Figure 4A:
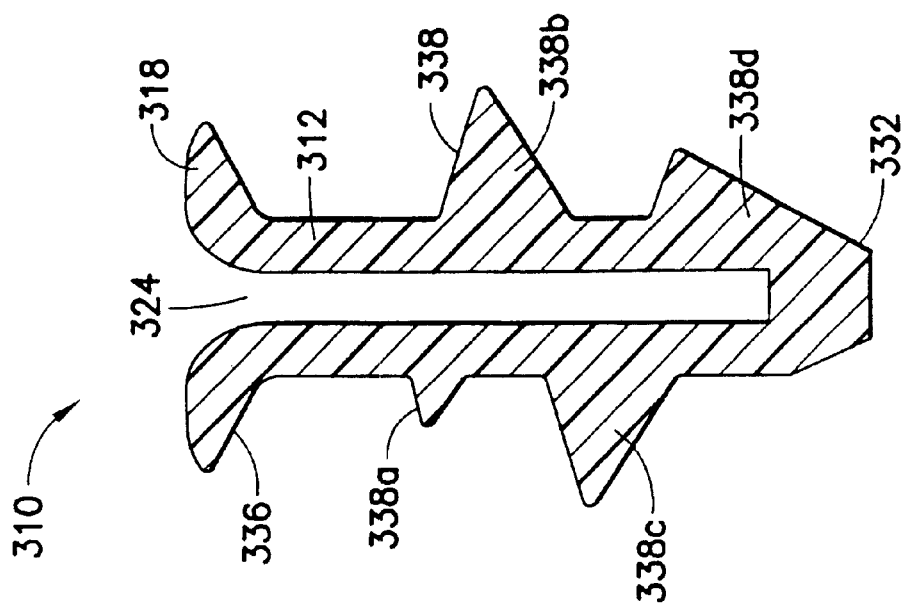
FIG. 4a is a perspective view of a third embodiment of a punctum plug according to the invention.
Figure 4A:
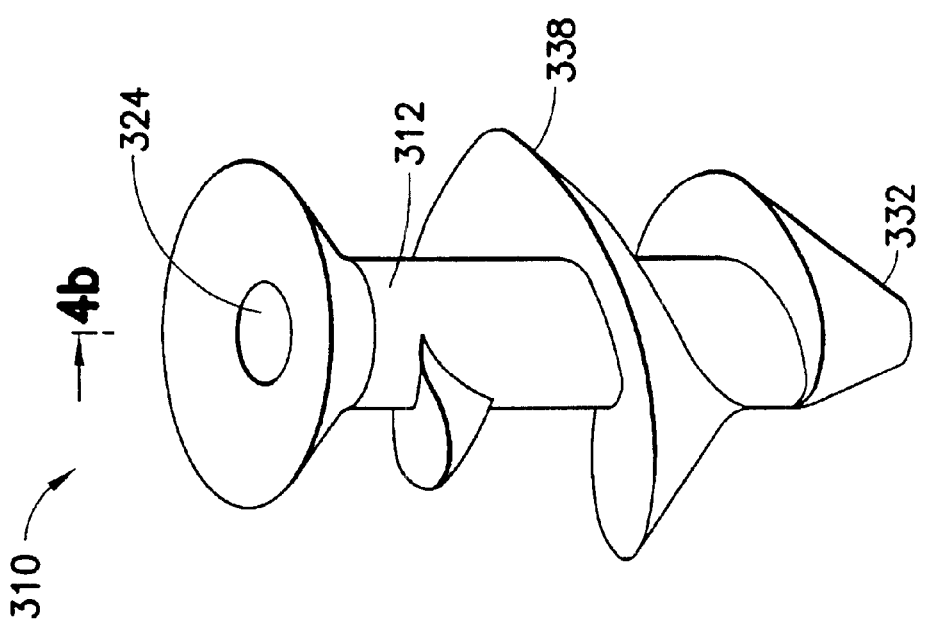

Referring to FIGS. 4a and 4b, a third embodiment of a punctum plug 310, substantially similar to the first embodiment 110 (with like parts having numbers incremented by 200) is shown. According to a third embodiment of the invention 310, the anchoring arm 338 is a single flange helically wound about (and integral with) the shaft 312 and preferably terminating distally at the tip 332 of the shaft 312. The helical flange 338 changes in radial length as it extends along the shaft, (e.g. compare portions 338b and 338c with portions 338a and 338d) with the helical flange 338 preferably extending the furthest radially at a midsection of the shaft 312. In addition, the helical flange preferably changes in pitch along the length of the shaft, with a longer pitch (steeper angle to the flange) nearer the tip 332, and a shorter pitch (with the flange more perpendicular relative to the shaft 312) nearer the head 318. The longer pitch at the tip 332 facilitates initial insertion of the plug 310 into the punctal opening, and the shorter pitch nearer the head 318 facilitates anchoring along the punctum. Slits (not shown) may be provided in the flange to facilitate folding of the flange within the punctum to accommodate insertion and varying punctal sizes. In addition, the spiralling flange 338 guides the punctum plug 310 into the punctal opening and aids in insertion by allowing the device to be inserted and positioned with a rotational (or screw-like) motion. To that end, the bore 324 is preferably provided with a non-circular cross-section (as taught in parent application U.S. Ser. No. 09/305,599) to receive an insertion tool having an interfering cross-section. As such, during insertion, rotation of the insertion tool results in corresponding rotation of the plug 310 to guide the plug 310 into the punctal opening. As with the previous two embodiments, at least a portion of the anchoring arm 338 (at 338b and 338c) extends radially a distance greater than the radial extension of the head 318.

Referring to FIGS. 5a and 5b, a fourth embodiment of a punctum plug 410 is shown. According to the fourth embodiment of the invention, two preferably radially arcuate (relative to the shaft) anchoring arms 438 are provided at a distal portion of the shaft 412 and extend outward and upwards towards the head 418. The anchoring arms 438 thereby function as barbs which operate to mechanically retain the plug within the punctum by engaging the punctal ring.

Referring to FIGS. 6a, 6b and 7, a fifth embodiment of a punctum plug 510 is shown. According to the fifth embodiment of the invention, a single anchoring arm 538 extends at an angle from the lower shaft 512 or tip 532 of the plug upward and outward, generally toward the periphery of the head 518 of the plug 510. In addition, the arm 538 is preferably relatively small adjacent the tip 532, to aid in insertion through the punctal opening, and generally becomes relatively larger with its distance from the tip. Referring to FIG. 7, the anchoring arm 538 is flexible, and adapted to bend upward 538a to facilitate insertion, and bend downward 538b once provided within the vertical punctum to engage the underside of the punctal ring 527 to secure the plug within the vertical punctum 528 via both frictional and mechanical engagement (FIG. 7).

The punctum,plugs of the invention are inserted into the punctum of a patient by optionally first dilating the punctal opening of the patient, inserting an insertion tool into the bore 124 (224, 324, 424, 524) of the plug, and positioning the tip 132 (232, 332, 432, 532) of the shaft 112 (212, 312, 412, 512) at the punctal opening. The plug is then moved either axially (in the case of plugs 110, 210, 310, 410, 510) or optionally axially with rotation (in the case of plug 310) through the punctal opening until the distal surface 136 (236, 336, 436, 536) of the head 118 (218, 318, 418, 518) of the plug rests against tissue at the punctal opening. The insertion tool is then removed from within the axial bore. The anchoring arms 138 (238, 338, 438, 538) frictionally or mechanically engage the punctal tissue and/or the punctal ring. As the punctal opening returns to its predilated state, the punctal tissue encloses about the shaft 112 (212, 312, 412, 512) and seats between the distal surface 136 (236, 336, 436, 536) of the tapered head 118 (218, 318, 418, 518) and the anchoring arms to secure the plug within the punctal opening and substantially completely blocking lacrimal fluid flow from entering the punctum.

According to the invention, the punctum plug is preferably designed to fit within a wide range of differently sized puncta. To this end, the punctum plug is preferably 1.5 mm to 2.5 mm long from head to tip. The shaft is preferably 1.4 mm to 2.4 mm long, and 0.4 mm to 0.6 mm in diameter. The head is preferably 1.5 mm to 2.5 mm in diameter (i.e. a diameter which is larger than a diameter of the largest punctal opening of a wearer). The radially extending anchoring arms preferably extend between 1.0 mm to 2.0 mm from the shaft with at least a portion of at least one of the anchoring arms extending beyond the radius of the head.

There have been described and illustrated herein several embodiments of a lacrimal flow occluder (punctum plug) and a method of inserting the occluder. While particular embodiments of the invention have been described, it is not intended that the invention be limited thereto, as it is intended that the invention be as broad in scope as the art will allow and that the specification be read likewise. Thus, while particular arrangements of anchoring arms have been disclosed, it will be appreciated that other arrangements may be used as well. For example and not by way of limitation, a punctum plug may have three or more offset flanges extending radially from the shaft Furthermore, while particular shapes, sizes, and numbers of the anchoring arms have been disclosed, it will be understood that punctum plugs having more or fewer anchoring arms formed about the shaft in a variety of shapes and sizes can be similarly used. Also, it will be appreciated that any of the embodiments may be formed having any style or shape tip. Further, while it is preferable that the anchoring bodies be spaced equidistance apart, it will be appreciated that the spacing can vary. In particular, in certain circumstances it may be desirable to provide additional distance between the largest arms and the arms adjacently above the largest arms. In addition, while particular types of materials have been disclosed, it will be understood other materials can be used.

Further, while it is preferred that the entire plug be formed from a flexible material, it will be understood that only portions of the plug (preferably the head and the anchoring arms) need be formed from a flexible material. It will therefore be appreciated by those skilled in the art that yet other modifications could be made to the provided invention without deviating from its spirit and scope as claimed.

What is claimed is:

1. A punctum plug for insertion into a punctum of a wearer, comprising:
   a) a shaft having a proximal end, a distal end, and a length;
   b) a plurality of circumferential rings radially extending from said shaft and spaced apart along said length of said shaft and defining spaces therebetween, at least one of said plurality of circumferential rings has a diameter larger than a diameter of said head; and
   c) a head at said proximal end of said shaft.

2. A punctum plug according to claim 1, wherein:
   said head and said shaft at least partially define an axial bore, said axial bore adapted to receive an insertion tool.

3. A punctum plug according to claim 1, wherein:
   at least one of said plurality of circumferential rings has a diameter larger than a diameter of said head.

4. A punctum plug according to claim 1, wherein:
   said plurality of circumferential rings include at least one proximal ring, one distal ring and an intermediate ring, at least two of said plurality of circumferential rings having different diameters.

5. A punctum plug according to claim 1, wherein:
   said head tapers distally toward said shaft.

6. A punctum plug according to claim 1, wherein:
   a tip is provided at said distal end of said shaft, said tip having a diameter no greater than a diameter of said shaft.

7. A punctum plug according to claim 6, wherein:
   said tip is one of pointed, rounded and truncated in shape.

8. A punctum plug according to claim 1, wherein:
   said shaft, said circumferential rings, and said head are flexible.

9. A punctum plug for insertion into a punctum of a wearer comprising:
   a) a shaft having a proximal end, a distal end, and a length;
   b) a plurality of circumferential rings radially extending from said shaft and spaced apart along said length of said shaft and defining spaces therebetween, said plurality of circumferential rings including at least one proximal ring, one distal ring and an intermediate ring, said intermediate ring having a larger diameter than said proximal ring and said distal ring; and
   c) a head at said proximal end of said shaft.

10. A punctum plug for insertion into a punctum of a wearer comprising:
    a) a shaft having a proximal end, a distal end, and a length;
    b) a plurality of circumferential rings radially extending from said shaft and spaced apart along said length of said shaft and defining spaces therebetween; and
    c) a head at said proximal end of said shaft, said head: said head having a concave proximal surface.

11. A punctum plug for insertion into a punctum of a wearer, comprising:
    a) a shaft having a proximal end, a distal end, a circumference, and a length;
    b) a plurality of flanges which extending less than 360 degrees about the circumference and are spaced apart along said length of said shaft; and
    c) a head at said proximal end of said shaft.

12. A punctum plug according to claim 11, wherein:
    said head and said shaft at least partially define an axial bore adapted to receive an insertion tool.

13. A punctum plug according to claim 11, wherein:
    said head has a radial extension and at least one of said flanges has a radial extension greater than said radial extension of said head.

14. A punctum plug according to claim 11, wherein:
    said plurality of flanges include at least a proximal flange, a distal flange and an intermediate flange, at least two of the flanges having different diameters.

15. A punctum plug according to claim 14, wherein:
    said intermediate flange is of a larger diameter than said proximal flange and said distal flange.

16. A punctum plug according to claim 11, wherein:
    said head tapers distally toward said shaft.

17. A punctum plug according to claim 11, wherein:
    a tip is provided at a distal end of said shaft, said tip having a diameter no greater than a diameter of said shaft.

18. A punctum plug according to claim 17, wherein:
    said tip is one of pointed, rounded and truncated in shape.

19. A punctum plug according to claim 11, wherein:
    said shaft, said plurality of flanges, and said head are flexible.

20. A punctum plug according to claim 11, wherein: said flanges are substantially semicircular.

21. A punctum plug for insertion into a punctum of a wearer comprising:
    a) a shaft having a proximal end, a distal end, a circumference, and a length;
    b) a plurality of flanges which are circumferentially offset and spaced apart along said length of said shaft; and
    c) a head at said proximal end of said shaft, said head; said head having a concave proximal surface.

22. A punctum plug for insertion into a punctum of a wearer, comprising:
    a) a longitudinally extending shaft having a proximal end, a distal end, and a length;
    b) a flexible flange radially extending from and helically coiled about said longitudinally extending shaft; and
    c) a head at said proximal end of said shaft.

23. A punctum plug according to claim 22, wherein:
    said head and said shaft at least partially define an axial bore adapted to receive an insertion tool.

24. A punctum plug according to claim 22, wherein:
    said flange has a portion which radially extends from said shaft greater than a maximum radial extension of said head.

25. A punctum plug according to claim 24, wherein:
    said flange has a proximal portion, a distal portion, and an intermediate portion, said intermediate portion being of larger radial extension than said proximal and distal portions.

26. A punctum plug according to claim 22, wherein:
    said head tapers distally toward said shaft.

27. A punctum plug according to claim 22, wherein:
    a tip is provided at a distal end of said shaft, said tip having a diameter which does not exceed a diameter of said shaft.

28. A punctum plug according to claim 27, wherein:
said tip is one of pointed, rounded and truncated in shape.

29. A punctum plug according to claim 22, wherein:
said shaft, said plurality of said flanges, and said head are flexible.

30. A punctum plug for insertion into a punctum of a wearer comprising:
   a) a shaft having a proximal end, a distal end, a length;
   b) a flange extending from and helically coiled about said shaft; and
   c) a head at said proximal end of said shaft,
      said head having a concave proximal surface.

31. A punctum plug for insertion into a punctum of a wearer, comprising:
   a) a shaft;
   b) anchoring means for anchoring said plug within the punctum, said anchoring means including at least one arm extending from said shaft at at least two axial locations along said shaft; and
   c) a head at a proximal end of said shaft.

32. A punctum plug according to claim 31, wherein:
said at least one anchoring means is at least one arm radially extending from said shaft.

33. A punctum plug according to claim 31, wherein:
said at least one anchoring means is at least one arm extending at an angle less than ninety degrees relative to said shaft.

34. A punctum plug according to claim 33, wherein:
said at least one arm forms a barb.

35. A punctum plug according to claim 34, wherein:
said barb is adapted to bend both toward said shaft and away from said shaft.

36. A punctum plug according to claim 34, wherein:
said at least one barb is curved.

37. A punctum plug according to claim 34, wherein:
said at least one arm include a portion which expands in size as said portion extends further from said shaft.

* * * * *